United States Patent [19]

Stang et al.

[11] Patent Number: 5,286,901

[45] Date of Patent: Feb. 15, 1994

[54] PRESCURSORS FOR AND SYNTHESIS OF MONO- AND DIFUNCTIONALIZED ACETYLENES AND DIFUNCTIONAL 1,3-DIYNES

[75] Inventors: Peter J. Stang; Charles M. Crittell; Bobby L. Williamson; Viktor Zhdankin, all of Salt Lake City, Utah

[73] Assignee: University of Utah Research Foundation, Salt Lake City, Utah

[21] Appl. No.: 732,663

[22] Filed: Jul. 19, 1991

Related U.S. Application Data

[63] Continuation-in-part of Ser. No. 491,328, Mar. 9, 1990, abandoned.

[51] Int. Cl.$^5$ .................................. C07C 309/00
[52] U.S. Cl. ................................. 562/40; 562/45; 562/83; 562/85
[58] Field of Search .................... 562/40, 45, 83, 85

[56] References Cited

U.S. PATENT DOCUMENTS 3,574,696 4/1971 Friedman et al. .
3,689,539 9/1972 Patmore et al. .
3,696,146 10/1972 Patmore et al. .
3,864,388 2/1975 Kitamura et al. .
4,322,432 3/1982 Roloff et al. .
4,347,346 8/1982 Eckberg .

OTHER PUBLICATIONS

Stang and Zhdankin, "Preparation and chemistry of PhI$^+$C≡CI$^+$Ph.2 O$^-$Tf . . . " *J. Am. Chemical Soc.* 113:4571–4576 (1991).
Zhdankin et al., "A general approach to unsymmetrical tricoordinate iodoninanes: single step preparation of mixed iodosobenzene . . . " *Tetrahedron Lett.* 31:4821–4824 (1990).
Stang and Zhdankin, "Bis[phenyl[(perfluoroalkanesulfonyl)oxy]-iodo]-1,3-butadiyne, PhI$^+$C≡CI$^+$Ph.2R$_f$SO$_3$ and 1.4-. . . ", *J. Am. Chem. Soc.* 112:6437–6438 (1990).
Segal et al., "The interaction of alkynyl carboxylates with serine enzymes," *FEBS Letters* 247:217–220 (Apr. 1989).
Stang and Kitamura, "Stereoselective formation of conjugated enynes via coupling of alkynyliodonium tosylates . . . ", *J. Am. Chem. Soc.* 109:7561–7563 (1987).

Allen et al., "Hydrolysis mechanisms of alkynyl benzoates, tosylates, and phosphates", *J. Am. Chem. Soc.* 110:622–624 (1988).
Stang et al., "Acetylenic esters. Preparation and mechanism of formation of alkynyl tosylates and mesylates via tricoordinate iodonium species", *J. Am. Chem. Soc.* 109:228–235 (1987).
Stang et al., "Acetylenic esters. Preparation and characterization of alkynyl carboxylates via polyvalent iodonium species", *J. Am. Chem. Soc.* 110:3272–3278 (1988).
Stang et al., "Acetylenic esters. Preparation and characterization of alkynyl dialkyl phosphates, RC≡COPO(OR)$_2$", *J. Am. Chem. Soc.* 111:2225–2230 (1989).
Kitamura and Stang, "Improved synthesis of alkynylphenyl- iodonium arylsulfonates (RC≡CIPh.OSO$_2$Ar)," *J. Organic Chem.* 53:4105–4106 (1988).

*Primary Examiner*—José G. Dees
*Assistant Examiner*—Joseph Conrad
*Attorney, Agent, or Firm*—Trask, Britt & Rossa

[57] ABSTRACT

Precursors and methods for the synthesis of mono- and difunctionalized acetylenes are described. The invention includes novel tricoordinate iodonium transfer reagents and novel alkynyldi(phenyliodonium) salts, both of which are precursors for the functionalized acetylenes. The iodonium transfer reagents take the general form of mixed iodonium sulfonates PhI$^+$(X$^-$)OSO$_2$R$_f$, where X may be OAc, NHAc, NCO, or CN. These mixed iodonium sulfonates are produced by reaction of iodosobenzene with certain substituted trimethylsilanes.

To make the alkynyldi(phenyliodonium) salt PhI$^+$-C≡CI$^+$Ph.2 R$_f$SO$_3^-$, a mixed iodonium sulfonate is reacted with a bistin acetylene of the kind R'$_3$SnC≡CSnR"$_3$. Alternatively, the reaction may be performed with disubstituted tin diacetylenes to produce PhI$^+$C≡C—C≡CI$^+$Ph.2 R$_f$SO$_3^-$ to produce a dialkynyldi(phenyliodonium) salt. Subsequent reaction of a nucleophile with the alkynyldi(phenyl-iodonium) salt or dialkynyldi(phenyliodonium) salt produces a difunctional acetylene or a difunctional 1,3-diyne, respectively.

11 Claims, No Drawings

PRESCURSORS FOR AND SYNTHESIS OF MONO- AND DIFUNCTIONALIZED ACETYLENES AND DIFUNCTIONAL 1,3-DIYNES

This invention was made with Government support under grant number 5R01CA16903 awarded by the National Institutes of Health. The government has certain rights in the invention subject to the provisions of 37 C.F.R. §401 and 45 C.F.R. §8.

BACKGROUND OF THE INVENTION

This application is a continuation-in-part of application Serial No. 07/491,328, filed Mar. 9, 1990, by Peter J. Stang, now abandoned.

FIELD

This invention relates generally to the organic chemical synthesis of functionalized acetylenes, and more specifically to tricoordinate iodonium compounds useful as precursors of mono- and di-functionalized acetylenes.

STATE OF THE ART

The known uses of acetylenic nitrates, phosphates, carboxylates, and sulfonate esters include silicone release coatings and inhibition of serine-based proteases as discussed in U.S. Pat. Nos. 3,864,388 and 4,322,432 and Segal et al., FEBS Letters 247:217-220, 1989, the contents of which are hereby incorporated by reference. Moreover, homopolymers of mono- and difunctionalized acetylenes have unusual optical properties which may soon be exploited in nonlinear optical devices. The functionalized acetylenes described in this application are defined as having the functional group directly attached to the acetylene.

Despite their usefulness, few functionalized acetylenes have yet been synthesized because no general and convenient processes have been found. Synthesis of difunctionalized acetylenes has been a particularly intractable problem. Standard procedures for acetylene synthesis do not work for most functionalized acetylenes.

A recent and promising approach to the synthesis of functionalized acetylenes employs polyvalent iodonium compounds. Alkynylphenyliodonium salts are one such type of compound. Alkynylphenyliodonium salts are also important precursors of conjugated enynes having defined stereogeometries (Stang and Kitamura, J. Am. Chem. Soc. 109: 7561-7563, 1987). Many important naturally-occurring compounds are stereo-defined conjugated enynes, including insect sex pheromones having well-known utility as pest control agents. Two examples of such pheromones which are conjugated enynes are the sex pheromone of Lepidoptera moths which defoliate pine trees (Guerrero et al., Tetrahedron Letters 22:2013-2016, 1981), and the sex pheromone of the European grape wine moth *Lobesia botrana* (Cassani et al., Tetrahedron Letters 24:2513-2516, 1983).

The parent application describes alkynyl(phenyl) iodonium trifluoromethanesulfonates, which are generally stable compounds which can be produced in relatively high yields. However, those compounds are useful primarily to synthesize mono-functionalized acetylenes.

Thus, there remains a need for a practical and general method to synthesize mono- and di-functionalized acetylenes.

Chemical Abbreviations

For convenience of notation, the following compounds or moieties are sometimes hereinafter shown or referred to as follows:
Trifluoromethanesulfonate: $TfO^-$, triflate or triflic;
Phenyl: Ph;
Iodonium: $I^+$;
p-Toluenesulfonate: $-OTs$; tosylate

SUMMARY OF THE INVENTION

Precursors and methods for the synthesis of mono- and difunctionalized acetylenes are provided by the invention. The invention includes novel tricoordinate iodonium transfer reagents and novel alkynyldi(-phenyliodonium) salts, both of which are precursors for the functionalized acetylenes. The iodonium transfer reagents take the general form of mixed iodonium sulfonates $PhI^+(X)^-OSO_2R_f$, where X may be OAc, NHAc, NCO, C≡N, or C≡CR1. The first four compounds, X=OAc, NHAc, NCO, or C≡N, have particularly utility in the synthesis of difunctionalized acetylenes. In the most preferred embodiment, X is CN and $R_f$ is $CF_3$. The mixed iodonium sulfonates are produced by reaction of iodosobenzene with the appropriate substituted trimethylsilanes.

Alkynylmono- or di-(phenyliodonium) salts which are immediate precursors to functionalized acetylenes are produced by reacting one of the mixed iodonium sulfonates with a mono- or di- tin-substituted acetylene to make alkynylmono- or di-(phenyliodonium) salts $R1C≡CI^+Ph·R_fSO_3^-$ or $PhI^+C≡CI^+Ph·2 R_fSO_3^-$, respectively. Diacetylene compounds having C≡C—C≡C in place of C≡C are also disclosed.

Reaction of the alkynylmono-or di-(phenyliodonium) salts with appropriate nucleophiles are useful to produce mono- or di-functional acetylenes, functionalized diynes and difunctional 1,3-diynes.

DETAILED DESCRIPTION OF THE INVENTION

Iodonium transfer reagents comprising mixed iodonium sulfonates are prepared by reacting iodosobenzene with a trimethylsilyl sulfonate in a mild chlorinated, polar solvent such as dichloromethane, followed by reaction with a trimethylsilyl derivative (reactions 1A and 1B).

(1A)

(1B)

Reactions (1A) and (1B) are a general method for producing any mixed iodonium sulfonate depending only on stability of the product E. Product E is an iodonium transfer reagent which is useful to transfer the iodonium moiety to tin-substituted acetylenes to form alkynyliodonium salts.

For stable products E it is found that reactant D should have an X group selected from the group including O-acetyl, NH-acetyl, NCO (isocyanate), C≡N, and C≡CR'. The respective products of reaction (1B) for these five X groups are:

$$PhI^+O-\overset{O}{\underset{\|}{C}}-CH_3.OSO_2R \quad (E1)$$

$$PhI^+NH-\overset{O}{\underset{\|}{C}}-CH_3.OSO_2R \quad (E2)$$

$$PhI^+N=C=O.OSO_2R \quad (E3)$$

$$PhI^+C\equiv N.OSO_2R \quad (E4)$$

$$PhI^+C\equiv CR'.OSO_2R \quad (E5)$$

Products E1 through E5 are stable and can be isolated in sufficient purity to be useful. Compounds with $X=N(CH_3)_2$, $ONH_2$, $N_3$, or $CH_2CN$, were found to decompose even at temperatures below 0° C. The R group of the trimethylsilyl sulfonate B may be $CF_3$, $n\text{-}C_4F_9$, or $p\text{-}CH_3C_6H_4$. In a preferred embodiment, B is trimethylsilyl trifluoromethane sulfonate, and the product E is then a mixed iodonium trifluoromethanesulfonate.

In a highly preferred embodiment, X is the cyano group $C\equiv N$. Compounds E4 appear to be the most stable and convenient of the compounds E for the subsequent uses described herein. In a further preferred embodiment, X is $C\equiv N$ and R is $CF_3$ or $C_4F_9$. The compound having $R=CF_3$ is somewhat preferred over that having $C_4F_9$, because the precursor compound is more available and less expensive. However, from the standpoint of usefulness and stability of the compound E4, the trifluoromethanesulfonate and the perfluorobutanesulfonate compounds are equivalent.

Intermediate C is believed to be similar to the Zefirov's reagent disclosed in the parent application, Ser. No. 07/491,328. In fact, when R in the sulfonate B is $CF_3$ and X in reactant D is an alkyne $C\equiv CR'$, products E5 are the previously disclosed alkynyl trifluoromethanesulfonates of the parent application (see reactions (2A) and (2C) below).

The sequence of reactions (1A) and (1B) is typically performed as follows: the iodosobenzene A and trimethylsilyl sulfonate B are mixed in equimolar quantities in a mild polar solvent such as methylene chloride or carbon tetrachloride at −30° C. under nitrogen. The mixture is warmed to −5° C. and stirred until a yellow homogeneous solution forms. This solution is recooled to −30° C., and D is added in an amount approximately equimolar to the starting quantity of B. The mixture is allowed to warm to from about −10° C. to about −5° C. and stirred for about an hour to form E, the iodonium transfer reagent, as a precipitate. The yields are generally between about 60% and about 95%, and the precipitate is recoverable in high purity (90% or more) by filtration.

In an alternate embodiment, reactant B is replaced with reactant B' triflic anhydride $(CF_3SO_2)_2O$. In this case, B' may be used in an amount of 0.5 molar equivalents relative to the amount of A. The product E' is a mixed iodonium trifluoromethanesulfonate.

$$\underset{A}{PhIO} + \underset{B'}{O(OSO_2CF_3)_2} \longrightarrow \underset{C'}{[\text{intermediate}]} \quad (2A)$$

$$\underset{C'}{[\text{intermediate}]} + \underset{D}{Me_3SiX} \longrightarrow \underset{E'}{PhI^+(X)OSO_2CF_3} \quad (2B)$$

If reactant D in reaction (2B) is an alkynyl compound D″ as shown in reaction (2C), the product is an alkynyl phenyliodonium trifluoromethanesulfonate F′. D″ is a silyl- or tin-substituted acetylene having the structure $A_3(Si \text{ or } Sn)C\equiv CR'$, where A is a lower alkyl such as methyl, ethyl or butyl, with methyl being preferred (reaction (2C) below).

$$\underset{C'}{[\text{int.}]} + \underset{D''}{A_3(Si \text{ or } Sn)C\equiv CR'} \longrightarrow \underset{F'}{R'C\equiv CPhI^+.OSO_2CF_3} \quad (2C)$$

Reaction 2A, 2C are also disclosed in the parent application Ser. No. 07/491,328. When reactions (2A) and (2C) are carried out in sequence, the reactants should be in proportions equivalent to their molar ratios in the equations, and the reaction may be performed at room temperature in mild polar solvents such as methylene chloride.

An alternate method of producing compounds F′ is to react E′ of reaction (2B) with D″, as shown:

$$\underset{E'}{PhI^+(X)OSO_2CF_3} + \underset{D''}{A_3(Si \text{ or } Sn)C\equiv CR'} \longrightarrow \quad (3)$$

$$\underset{F'}{R'C\equiv CPhI^+.OSO_2CF_3}$$

More generally, reaction of E with D″:

$$\underset{E}{PhI^+(X)OSO_2R} + \underset{D''}{A_3(Si \text{ or } Sn)C\equiv CR'} \longrightarrow \quad (4)$$

$$\underset{F}{R'C\equiv CPhI^+.OSO_2R}$$

In principle in reactions (2C), (3) and (4), group R′ of reactant D″ may be any organic group which does not interfere with the respective reaction. Accordingly, the invention is considered to encompass mono-phenyliodonium acetylenes F and F′ having any R′ group available from a trialkyltin- or trialkylsilyl-acetylene, subject only to the requirement that R′ not interfere with the appropriate reaction (2C), (3), or (4).

Possible groups R′ include H, lower alkyl groups, and lower aryl or arylalkyl groups such as phenyl and lower heterocyclic groups. For the purpose of this application, "lower alkyl" is defined as $CH_3(CH_2)_n$ where n is an integer $\leq 20$. Group R′ may also be a functional group such as a halogen, keto, amino, alkoxy, silyl, trialkylsilyl including methylsilyl, or alkyl-$O$-$CH_2$ where the $CH_2$ is attached to the triple-bonded carbon. In these cases, interference of the R′ moiety with reactions (2C), (3) or (4) is less likely if the alkyl group is a lower alkyl as defined previously. However, it is believed that R′ need not be limited to 20 carbons and may include peptide molecules. A peptide could be linked by its terminal amino group to the acetylene moiety.

Many silicon- or tin-substituted acetylenes D, D" are available commercially, for example from Aldrich Chemicals. Those not available commercially are easily synthesized (see for example *Preparative Acetylenic Chemistry*, L. Brandsma, Elsevier, N.Y., 1988).

Examples of compounds F and F' which have been synthesized to date include those having the following functional groups attached as R' to the acetylenic carbon (reactions 2C, 4 and 5) include the following:

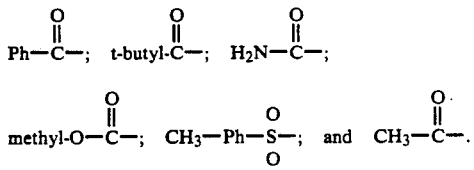

EXAMPLE I

Ten millimoles of trimethylsilyl trifluoromethanesulfonate were added to a stirred suspension of 10 millimoles of PhIO in 30 milliliters of dichloromethane at −30° C. under nitrogen. The mixture was allowed to warm to −5° C. and stirred until a yellow homogenous solution had formed. This solution was recooled to −30° C., and 11 millimoles of trimethylsilylcyanide dissolved in 30 milliliters of dichloromethane was added. The mixture was again allowed to warm to between about −10° and −5° C. and stirred for about one hour. A crystalline solid formed and was filtered under nitrogen. The precipitate was washed with cold ether and dried in vacuo. The resulting material was shown to be cyanophenyliodonium trifluoromethanesulfonate formed at a yield of about 89%, and a purity of >90%. The spectral analysis revealed IR peaks (selected absorptions in $CCl_4$, $cm^{-1}$) at 2182 (C≡N), 1294, 1257, 1208, 1182, 1034 (−OTf). $^1$H NMR ($\delta$, $CD_3CN$, in ppm): 8.3–8.4 (m, 2H), 7.9–7.8 (m, 1H), 7.75–7.65 (m, 2H). $^{13}$C NMR ($\delta$, $CD_3CN$, in ppm): 137.1, 135.6, 134.6, 119.6 (pH); 120.8 (d, J=118 Hz, $CF_3$), 68.3 (CN). $^{19}$F NMR ($\delta$, $CD_3CN$, in ppm): −76.5 ($CF_3$).

EXAMPLE II

The procedure substantially according to Example I was performed, except that trimethylsilyl p-toluenesulfonate was employed in place of trimethylsilyl trifluoromethanesulfonate. The product isolated in a 91% yield was shown to be cyanophenyliodonium toluenesulfonate. The melting point was 108° C. Spectral analysis: IR peaks (selected absorptions in $CCl_4$, $cm^{-1}$) at 2167 (C≡N), 1266, 1133, 1104, 989 (OTs). $^1$H NMR ($\delta$, $CD_3CN$, in ppm): 8.2–7.2 (m, 9H), 3.1 (s, 3H). $^{13}$C NMR ($\delta$, $CD_3CN$, in ppm): 146.0, 139.5, 137.9, 131.2, 129.1, 128.3, 126.3, 118.1, (Ar); 94.7 (CN); 21.3 ($CH_3$).

EXAMPLE III

The procedure substantially according to Example I was performed, except that trimethylsilyl acetate was used in place of trimethylsilyl cyanide. The product isolated in a 78% yield was shown to be acetoxyphenyliodonium trifluoromethanesulfonate The melting point was 91° C. IR spectral analysis (selected absorptions in $CCl_4$, $cm^{-1}$): 1721 (CO), 1280, 1229, 1169, 1053, 1031 (OTf and OAc). $^1$H NMR ($\delta$, $CD_3CN$, in ppm): 8.3–8.2 (m, 2H); 7.8–7.6 (m, 1H); 7.6–7.5 (m, 2H); 2.1 (s, 3H). $^{13}$C NMR ($\delta$, $CD_3CN$, in ppm): 175.0 (CO); 137.6, 135.3, 132.9 (pH); 120.5 (d, J=118 Hz, $CF_3$); 18.5 ($CH_3$). $^{19}$F NMR ($\delta$, $CD_3CN$, in ppm): −78.0 ($CF_3$).

This compound was very unstable and may therefore be of limited utility.

EXAMPLE IV

The procedure substantially according to Example I was performed, except that trimethylsilylperfluorobutane sulfonate was used in place of trimethylsilyl trifluoromethanesulfonate. The product isolated in an 84% yield was shown to be cyanophenyliodonium perfluorobutane sulfonate with a melting point of 124° C. IR spectral analysis (selected absorptions in $CCl_4$, $cm^{-1}$): 2181 (CN); 1301, 1210, 1140, 1010, 985 (ONf). $^1$H NMR ($\delta$, $CD_3CN$, in ppm): 8.3–8.4 (m, 2H); 7.9–7.8 (m, 1H); 7.7–7.6 (m, 2H). $^{13}$C NMR ($\delta$, $CD_3CN$, in ppm): 136.5, 134.9, 133.9, 103.0 (pH); 119 (br. m, $C_4F_9$); 68.5 (CN). $^{19}$F NMR ($\delta$, $CD_3CN$, in ppm): 4.8 (m, 2F); −2.2 (m, 2F); −6.6 (m, 2F); −81.2 (t, 3F).

EXAMPLE V

The procedure substantially according to Example I was performed, except that trimethylsilyl acetylamine was used in place of trimethylsilyl cyanide. The resulting product, formed in a yield of 97%, had a melting point of 167° C. and was shown to be acetylaminophenyliodonium trifluoromethanesulfonate. IR spectral analysis (selected absorptions in $CCl_4$, $cm^{-1}$): 3280 (NH); 1673 (CO); 1255, 1173, 1030 (OTf). $^1$H NMR ($\delta$, $CD_3CN$, in ppm): 8.5 (br. s, 1H); 8.3–8.2 (m, 2H); 7.7–7.6 (m, 1H); 7.4–7.2 (m, 2H); 2.1 (s, 3H). $^{13}$C NMR ($\delta$, $CD_3CN$, in ppm) 172.6 (CO); 136.2, 134.1, 132.4, 118.3 (pH); 120.9 (d, J=118 Hz, $CF_3$); 20.4 ($CH_3$). $^{19}$F NMR ($\delta$, $CD_3CN$, in ppm): −78.6 ($CF_3$).

EXAMPLE VI

The procedure substantially according to Example I was performed, except that trimethylsilyl isocyanate was substituted for trimethylsilyl cyanide. The resulting product isolated in a 51% yield was shown to be isocyanophenyliodonium trifluoromethanesulfonate, PhI+N≡C=O·TfO. IR spectral analysis (selected absorptions in $CCl_4$, $cm^{-1}$): 2506, 1622 (NCO); 1259, 1174, 1024 (OTf). $^1$H NMR ($\delta$, $CD_3CN$, in ppm): 8.3–7.5 (m). $^{13}$C NMR ($\delta$, $CD_3CN$, in ppm): 172.5 (CO); 136.6, 135.0, 132.8, 122.7 (pH); 120.8 (d, J=118 Hz, $CF_3$). $^{19}$F NMR ($\delta$, $CD_3CN$, in ppm): −78.6 ($CF_3$). This product was very unstable and therefore may prove to have little utility.

EXAMPLE VII

Ten millimoles (2.2 grams) of iodosobenzene was mixed with 5 millimoles (0.84 milliliters) of trifluoromethanesulfonic anhydride in 25 milliliters of methylene chloride. After being reacted for 10 minutes at 0° C., the resulting solution was further reacted with 10 millimoles (3.59 grams) of 3-methoxy-1-propyne in 25 milliliters of methylene chloride, for 30 minutes at 0° C. After concentration in vacuo and addition of diethyl ether a tan crystalline product was precipitated which had a melting point of 66°–67° C.(dec). Infrared and multinuclear NMR spectra data demonstrated that the product was the expected 3-methoxy-1-propynyl(phenyl)iodonium trifluoromethanesulfonate. The yield was 1.78 grams or 42%. Propynyl methoxybenzoate, which is readily prepared from this compound via reactions (11) and (12), has been shown to have utility as an inhibitor of serine-type proteases such as chymotrypsin, pronase, thrombin and plasmin (Segal et al. 1989)

The iodonium transfer reagents E, E', and F produced in reactions (1B), (2B), and (2C) respectively, are useful to transfer the iodonium moiety to a tinacetylenes and bistinacetylenes as illustrated in reactions (5) through

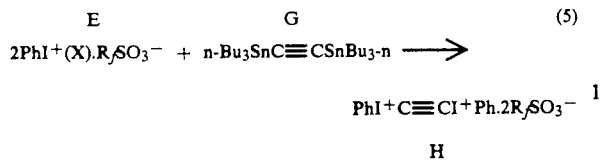

It should be noted that F or F' may be substituted for E resulting in either case in the product $H'=R'C\equiv CI^{+-}$ $Ph \cdot OSO_2R_f^-$. Compounds H, H' are alkynyl di- and mono-(phenyliodonium) sulfonates, respectively. Where the first reactant is E or E', reaction (5) is carried out in mild polar chlorinated solvents such as methylene chloride or chloroform at temperatures of around $-20°$ to $-30°$ C. If the first reactant is F' or F, reaction (5) may be performed at about room temperature in a mild polar solvent.

In a preferred embodiment, group X in compound E is $C\equiv N$. In a highly preferred embodiment, $R_f$ is $CF_3$ (see Example VII).

Bisphenyliodonium sulfonates H are formed in moderate to high yields, typically 60-90%. They are readily recovered by standard workup procedures such as, but not limited to, precipitation from the solvent by addition of diethyl ether. After washing again in ether, the product sulfonates are usually sufficiently pure for use in the synthesis of functionalized acetylenes as described later herein.

Other bis-trialkyltinacetylenes besides the bis (tributyltin)acetylene G may be used in reaction (5). Trimethyltinacetylene and triethyltinacetylene both give similar results to the tributyltinacetylene. However, the methyl compound is somewhat more toxic. The bis tributyl tinacetylene is both readily available and easy to handle, and therefore is somewhat preferred.

EXAMPLE VIII

A solution of containing 5 millimoles (3.02 grams) of bis(tributyltin)acetylene in 20 milliliters of dichloromethane was added to 100 milliliters of a stirred suspension of [cyano(trifluoromethanesulfonyloxy)iodo] benzene (10 millimoles; 3.79 grams) at $-78°$ C. under nitrogen. The mixture was brought to about 0° C. and stirred for 10 minutes until a white microcrystalline precipitate formed. The precipitate was filtered under nitrogen, washed with 100 milliliters of dichloromethane, and dried in vacuo. The precipitate was shown by spectral analysis to be di[phenyl(trifluoromethanesulfonyloxy)iodo] acetylene, recovered at a yield of 81% and having a melting point of 127°-128° C. IR spectral analysis (selected absorptions in $CCl_4$, $cm^{-1}$): 3095, 1581, 1560, 1281, 1237, 1217, 1169, 1025, 985. Raman spectrum (neat, $cm^{-1}$): 2137. $^1H$ NMR ($\delta$, $CD_3CN$, in ppm): 7.55-7.65 (m, 2H); 7.7-7.8 (m, 1H); 8.1-8.2 (m, 2H). $^{19}F$ NMR ($\delta$, $CD_3CN$, in ppm): $-78.93$ (s, $CF_3$). $^{13}C$ NMR ($\delta$, $CD_3CN$, in ppm): 51.84 ($C\equiv C$); 120.5 (quart. J=318 Hz, $CF_3$); 123.6, 133.8, 134.6, 136.2 (pH). HRMS calculated for $C_{16}H_{10}I_2O_6S_2F_6$: C, 26.32; H, 1.38; S, 8.78. Observed: C, 26.27; H, 1.39; S, 8.84.

Phenyliodonium and bis(phenyliodonium) diacetylene triflates may be prepared using the iodonium transfer reagent E in reactions (6) or (7), respectively. Reaction (6) and Example IX describe synthesis of a (phenyliodonium) diacetylene triflate:

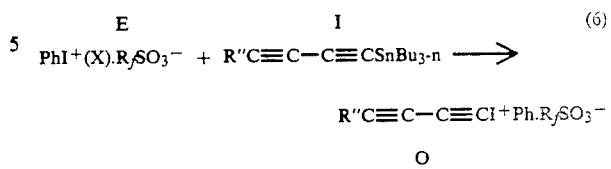

A general procedure for synthesis of 1,3-diynylphenyliodonium triflates is to prepare one equivalent of cyano(phenyliodonium) trifluoromethane sulfonate in dichloromethane (30 milliliters/millimole) under nitrogen at $-40°$ C. A solution of 1 equivalent of metal-substituted acetylene in dichloromethane (5 milliliters/millimole) is added dropwise. Procedure 1) The reaction mixture is allowed to warm to room temperature, then concentrated under reduced pressure to yield a yellowish oil. A white powder product is precipitated by adding the oil to vigorously stirred hexane at room temperature. The solvent is decanted, and the powder washed twice with additional hexane and dried in vacuo (room temperature, 1 Torr). Alternatively, depending on the reactant I, Procedure 2) is employed. The reaction mixture is kept at $-40°$ C. and hexane cooled to $-40°$ C. is added. The resulting white precipitate is washed with additional hexane, dried in vacuo at $-30°$ C., 1 torr, and stored at temperatures below $-20°$ C. Procedure 1 is applicable to the reaction with I=trimethylsilyl tributyltin diacetylene, tert-butyl tributyltin diacetylene, or methyl tributyltin diacetylene. Procedure 2 is required for I=n-butyl tributyltin diacetylene or phenyl tributyltin diacetylene.

EXAMPLE IX (5,5-dimethyl-1,3-hexadiynyl)tri-n-butylstannane was reacted with cyano(phenyliodonium) triflate as described in the preceding paragraph, with the product workup according to procedure 1) producing an 84% yield of 5,5-dimethyl-1,3-hexadiynyl(phenyliodonium) triflate.

(5,5-dimethyl-1,3-hexadiynyl)tri-n-butylstannane was synthesized as follows a solution containing ethylmagnesium bromide (19.3 millimoles) and 5,5-dimethyl-1,3hexadiyne (19.3 millimoles) in 50 milliliters of ether was refluxed for 5 hours under nitrogen, then cooled to $-78°$ C. To this solution, 18.6 millimoles of tri-n-butyltin chloride in 10 milliliters of ether was added slowly. The reaction mixture was allowed to warm to room temperature and stirred for 16 hours. Water was added to form a two-phase mixture, the phases were separated, and the aqueous phase was washed with ether. The ether wash was combined with the organic phase from the initial phase separation, and evaporated under reduced pressure to yield a crude oil. Distillation in vacuo produced 2.92 grams of pure (5,5-dimethyl-1,3-hexadiynyl)tri-n-butylstannane.

Spectral data confirming the product 5,5-dimethyl-1,3-hexadiynyl(phenyliodonium) triflate were as follows. IR ($cm^{-1}$): 3085, 3063, 2974, 2954, 2930, 2868, 2244, 2203, 2113, 1560, 1472, 1458, 1446, 1290, 1231, 1217, 1171, 1022, 737. $^1H$ NMR ($CD_2Cl_2$, $\delta$, 300 MHz): 1.18 (s, 9H, $CH_3$); 7.63 (t, 2H, J=7.8, $H_{meta}$); 7.68 (t, 1H, J=7.3, $H_{para}$); 8.06 (d, 2H, J=8.3, $H_{ortho}$). $^{13}C$ NMR ($CD_2Cl_2$, $\delta$, 75 MHz): 20.1 (s,$I-C\equiv$), 28.1 (s, $C(CH_3)_3$), 29.7 (s, $CH_3$), 62.7, 90.4, 94.5 (3s, $C\equiv$), 116.6 (s, $C_{arom}$), 119.5 (q, $J_{C-F}$=318, CF$_3$), 132.4, 132.9, 134.6 (3s, CH$_{arom}$).

Reaction (7) and Examples X through XIX illustrate the synthesis of bis(phenyliodonium)diacetylene triflates.

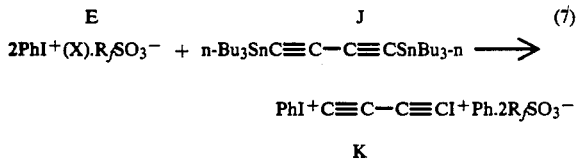

$$2PhI^+(X).R_fSO_3^- + n\text{-}Bu_3SnC\equiv C-C\equiv CSnBu_{3-n} \longrightarrow$$
$$PhI^+C\equiv C-C\equiv CI^+Ph.2R_fSO_3^-$$
$$K$$

Reactant J, bis(tributyltin)diacetylene, is readily prepared by a known method from dilithium acetylide and tri-butyltin chloride (C. Cauletti et al, Gazz. Chim. Ital. 118:1, 1988). The bisphenyliodonium diacetylenes K can be produced using procedures essentially the same as for the corresponding bisphenyliodonium monoacetylene. However, the bis diacetylenes K may be much less stable than the monophenyl diacetylenes, and must generally be handled at temperatures below about −10° to −20° C. to prevent decomposition.

The alkynyliodonium sulfonates which are the products of reactions (5) through (7) are useful to synthesize functionalized acetylenes. Difunctionalized acetylenes can be made by reacting the bis(phenyliodonium)acetylene sulfonate H of reaction (5) with an appropriate nucleophile, as illustrated in Examples X through XVII. The range of nucleophiles which can be employed is limited primarily by the stability of the product of the reaction. Nucleophiles which are presently known or believed to give stable, isolatable products include thiophenolate salts, lithium phenoxide, triaryl phosphines, trialkyl phosphines, alkoxides, and metal carbonyl anions.

EXAMPLE X

Sodium thiophenolate (0.15 grams, 1.1 millimoles) was added to a suspension containing 0.365 grams (0.5 millimoles) of the bis(phenyliodonium) acetylene H in 20 milliliters of CH$_3$CN at −35° C. under nitrogen. The mixture was stirred for 1 hour at −35° C. until a yellow solution had formed. The solution was then warmed to room temperature and concentrated in vacuo. The residue, which included crystals of NaOTf (sodium trifluoromethane sulfonate) in oil, was treated with 30 milliliters of dichloromethane and the insoluble NaOTf was filtered off. The filtrate was concentrated and chromatographed on silica gel with hexane as the eluent. 80 milligrams (66% yield) of a colorless oil was recovered and was shown to be di(phenylthio)acetylene. The spectral results were: IR peaks (the neat oil), 3058, 1579, 1477, 1023, 735 and 687 cm$^{-1}$; $^1$H NMR ($\delta$, CDCl$_3$), 7.2-7.4 (m, 3H), 7.5-7.6 (m, 2H); $^{13}$C NMR ($\delta$, CDCl$_3$), 87.98 (C≡C), 126.03, 127.11, 129.28, 133.27 (pH). Mass spectrum (FAB): m/z (%) 242 (80), M+; 139 (30), [PhSC2]; 109 (53), [PhS]+. HRMS for C$_{14}$H$_{10}$S$_2$(M+): calculated wt. 242.02239, observed wt. 242.02212.

EXAMPLE XI

One milliliter of a 2.5 molar solution of butyl lithium in hexane was added to 25 milliliters of dichloromethane containing 0.235 grams (2.5 millimoles) of phenol at −30° C. under nitrogen. The solution was stirred and a white precipitate of LiOPh immediately formed. The mixture was cooled to −78° C. and 1 millimole of the bis[phenyliodonium] acetylene H was added. The mixture was stirred for 15 minutes at −78° C. and then allowed to warm to room temperature, producing a dark solution. The solution was filtered through 5 grams of silica gel, and the solvent was evaporated. The filtrate was then chromatographed on 50 grams of silica gel with hexane as the eluent, producing 0.12 grams of a colorless oil which was shown to be di(phenoxy)acetylene. Spectral analysis was as follows: IR (the neat oil), peaks at 3061, 1591, 1489, 1452, 1376, 1214, 747 cm$^{-1}$; $^1$H NMR ($\delta$, CDCl$_3$), 7.2-7.4 m. $^{13}$C NMR ($\delta$, CDCl$_3$), 116.7 (C≡C), 122.6, 123.0, 124.9, 129.6 (pH). Mass spectrum (EI, 70 eV): m/z (%) 210 (100), M+. HRMS for C$_{14}$H$_{10}$S$_2$ (M+): calculated, 210.06808; observed 210.06637.

EXAMPLE XII

A mixture containing two millimoles of bis(phenyliodonium)acetylene trifluoromethanesulfonate and 3.8 millimoles of Ph$_3$P in 30 milliliters of dry CCl$_4$ was stirred for 20 hours at room temperature under nitrogen. To avoid unwanted byproducts, it was extremely important that the solvent (carbon tetrachloride) be absolutely anhydrous. A white solid formed and was filtered under nitrogen and treated with fifty milliliters of CH$_2$Cl$_2$. Unreacted iodonium salt starting material which was insoluble in CH$_2$Cl$_2$ was filtered off, and the filtrate concentrated and crystallized by addition of ether. 0.99 grams (59%) of di[triphenyl(trifluoromethanesulfonyloxy) phospho]acetylene was recovered and additionally purified by several recrystallizations from CH$_2$Cl$_2$-ether. The product was extremely hygroscopic and water sensitive, so all of the latter operations were performed under dry nitrogen. (Exposure of the crystalline product to air caused it to degrade rapidly to an unidentified orange oil.) The melting point was 164°-166° C. (dec), and the spectral analysis as follows: melting point 164°-166° C., IR (CCl$_4$): peaks at 3055, 1584, 1486, 1435, 1286, 1105, 1024, 863, 795 cm$^{-1}$. $^1$H NMR ($\delta$, CDCl$_3$):7.7-7.9 (m). $^{19}$F NMR ($\delta$, CDCl$_3$): −78.6 (s, CF$_3$). $^{31}$P NMR ($\delta$, CDCl$_3$): 11.84 (s). $^{13}$C NMR ($\delta$, CDCl$_3$):120.5 (quart. J=318 Hz, CF$_3$), 114.05 (d, J=90 Hz), 131.1, 134, 136.9 (all m, Ph), 135.15 (d, J=100 Hz, C≡C). Mass spectrum (FAB): m/z (%) 698 (4), [M−TfO−]+; 565 (11), [M−TfO−−−$SO_2$CF$_3$]+; 550 (3), [M−2TfO−]+; 279 (100), [Ph$_3$POH]+. HRMS for C$_{38}$H$_{31}$OP$_2$ [M−TfO- -SO$_2$CF$_3$+H+]+: calculated 565.18502, observed, 565.18697.

EXAMPLE XIII

A mixture containing 0.5 millimoles (0.365 grams) of bis(phenyliodonium) acetylene trifluoromethanesulfonate and 0.53 millimoles (0.14 grams) of Ph$_3$P in 10 milliliters of CCl$_4$ was stirred for three hours under nitrogen at room temperature. (As with the reaction of Example XII, it was extremely important that the solvent be anhydrous to avoid an undesired side reaction forming an olefin.) The solvent was decanted and the residue in the flask was washed with an additional 20 milliliters of dry CCl$_4$. The residue was then treated with 20 milliliters of dry dichloromethane. Unreacted starting salt H which was insoluble in the dichloromethane was filtered off, and the filtrate was concentrated to give 0.3 grams (a 76% yield) of PhI+C≡CP+Ph$_3$ 2 $^{31}$ OTf. The product was further purified by low-temperature recrystallization (crystal form below 0° C.) from dichloromethane-ether. All of these operations were performed under dry nitrogen. Spectral data: IR (neat oil, cm$^{-1}$), 3064, 2066 (C≡C), 1587, 1441, 1260, 1030; $^1$H NMR (δ, CDCl$_3$) 7.55-5.93 (m); $^{19}$F NMR (δ, CDCl$_3$) −78.1 (s, CF$_3$); $^{31}$P NMR (δ, CDCl$_3$) 7.6 (s); $^{13}$C NMR (δ, CDCl$_3$) 64.5 (d, J$_{C-P}$=178 Hz, C≡CP$^+$), 120.1 (quart, J=319 Hz, CF$_3$), 125.9 (d, J=107 Hz, C≡CI$^+$), 110.8 (d, J=29 Hz), 116.7 (d, J=100 Hz), 129.0, 130.4, 131.8, 132.9, 133.7, 135.9 (all m, Ph); mass spectrum (FAB) m/z (%) 287 (100) [M+H$^+$−2TfO$^-$−PhI]$^+$; HRMS for C$_{20}$H$_{16}$P [M+H$^+$−2 TfO$^-$−PhI]$^+$ calculated 287.09896, observed 287.09986.

EXAMPLE XIV

One millimole of the silyl enol ether of acetophenone was added to a stirred suspension containing ½ millimole of bis(phenyliodonium) salt in 20 milliliters of CH$_3$CN at −35° C. under nitrogen. The mixture was allowed to warm to room temperature over a period of about 15 minutes, resulting in a dark yellow solution. The solvent was evaporated and the remaining solution was chromatographed on silica gel and eluted with methylene dichloride to yield 0.11 grams of a yellow oil which was shown to be 1,6-diphenylhexa-2,3-diene-1,6-dione. The spectral analysis was as follows: IR (the neat oil) peaks at 3058, 2982, 1955, and 1925 (C=C=C), 1654 and 1652 (C=O), 1597, 1463, 1430, 1314, 1298, 1216, 1177, 1032, 862, 756, 729, 652 cm$^{-1}$. $^1$H NMR (δ, CDCl$_3$): 5.3 (br. s, 2H, CH$_2$), 7.05 (qd, J=6.7 and 2.6 Hz, 1H, CH), 7.4 (d, J=6.7 Hz, 1H, CHCO), 7.6-7.4 (m, 6H, Ph), 8.0-7.9 (m, 4H, Ph). $^{13}$C NMR (δ, CDCl$_3$): 112.32, 116.44, 127.97, 128 23, 129.61, 131.24, 132.37, 132.44 (2Ph), 137.59 (CH), 139.19 (CH), 192.06 (=C=), 216.3 (2C=O). Mass spectrum (FAB): m/z (%) 105 (100), [PhCO]$^+$.

Bis(phenyliodonium) diene cycloadducts having specific isomeric configurations can also be produced by reaction of the bis(phenyliodonium) acetylene H with cyclic and heterocyclic compounds including pentadienes and furans. Reactions (8) through (10) are typical. Because of the high reactivity and easy substitution of the iodonium moiety, reaction of the bis(phenyliodonium) dienes with appropriate nucleophiles will be useful to produce diverse functionalized norbornadienes.

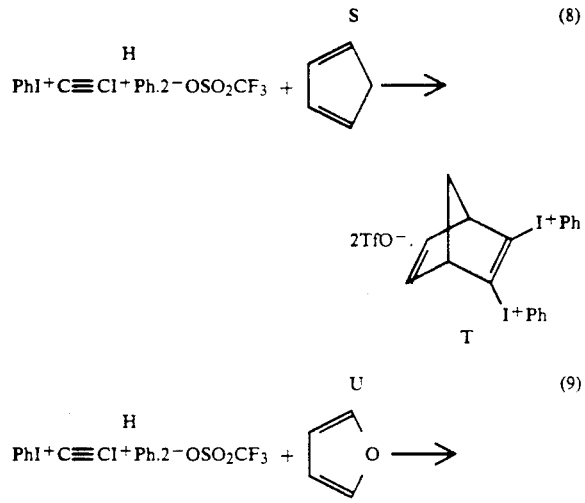

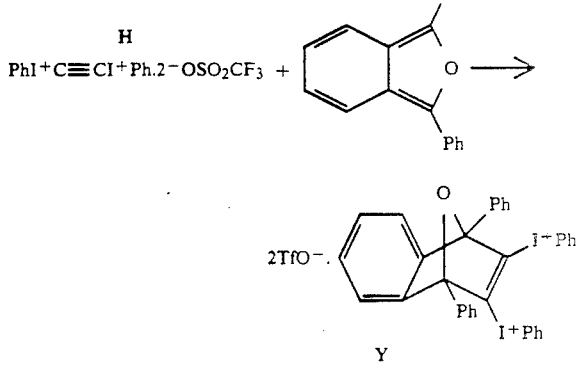

A general procedure for reactions of the type illustrated by (8) through (10) is as follows. A solution containing 2 millimoles of the appropriate diene in 20 milliliters of CH$_3$CN is added to a stirred suspension containing 1 millimole of the bis(phenyl-iodonium) salt in 20 milliliters of CH$_3$CN at −35° C. under nitrogen. The mixture is warmed to room temperature and then stirred for about one hour. The resulting solution, which may be yellow, is concentrated to a small volume, perhaps 1/20 to 1/40 of the starting volume, and crystallized by addition of 20 milliliters of methylene dichloride and 10 milliliters of ether. The crude crystallized products may be further purified by recrystallization from CH$_3$CN-CH$_2$Cl$_2$-ether, and dried in vacuo. Examples XIV through XVI are illustrative.

EXAMPLE XV

One hundred thirty milligrams of cyclopentadiene reacted by the above procedure yielded 0.55 grams of di[phenyl(trifluoromethanesulfonyloxy)iodo]norbornadiene. X-ray quality single crystals were obtained by slowly evaporating a solution of T in CH$_3$CN in an open air container. The product was shown to have a melting point of 177°–179° C. (dec). Spectral anylysis was: IR (CCL$_4$, cm$^{-1}$), 3087, 3065, 1568, 1472, 1445, 1281, 1242, 1225, 1204, 1162, 1022, 984. $^1$H NMR (δ, CD$_3$CN): 2.02 (m, 1H, H-7 anti), 2.42 (m, 1H, H-7 syn), 3.99 (m, 2H, H-3 and H-6), 6.31 (m, 2H, H-4 and H-5), 7.59 (m, 2H, Ph), 7.62 (m, 1H, Ph), 8.01 (m, 2H, Ph). $^{19}$F NMR (δ, CD$_3$CN): −77.8 (s, CF$_3$). $^{13}$C NMR (δ, CD$_3$CN): 61.9 (C-3 and C-6), 76.2 (C-7), 121.3 (quart. J=319 Hz, CF$_3$), 112.5, 133.4, 134.2, 137.0 (pH), 139.2 (C-1 and C-2), 141.4 (C-4 and C-5). HRMS calculated for C$_{21}$H$_{16}$F$_6$I$_2$O$_6$S$_2$: C, 31.67; H, 2.03;, S, 8.05. Observed values: C, 31.76; H, 2.06; S, 7.95.

EXAMPLE XVI

One hundred forty milligrams of furan was reacted by the above procedure yielding 0.58 grams (73%) of di[phenyl (tirfluoromethanesulfonyloxy)iodo]-3,5-epoxy-1,4-cyclohexadiene having a melting point of 118°–119° C. (dec). Spectral analysis was: IR (CCl$_4$, cm$^{-1}$): 3093, 3065, 1566, 1472, 1445, 1279, 1242, 1168, 1021, 885, 868. $^1$NMR (δ, CD$_3$CN): 5.62 (br. s 2H, H-3 and H-6), 6.75 (br. s, 2H, H-4 and H-5), 7.62 (m, 2H, Ph, 7.81 (m, 1H, Ph), 8.05 (m, 2H, Ph). $^{19}$F NMR (δ, CD$_3$CN): −77.85 (s, CF$_3$). $^{13}$C NMR (δ, CD$_3$CN): 90.8 (C-3 and C-6), 121.2 (quart. J=319 Hz, CF$_3$), 112.4, 133.6, 134.5, 137.1 (pH), 139.2 (C-1 and C-2), 142.7 (C-4 and C-5). HRMS calculated for C$_{20}$H$_{14}$F$_6$I$_2$O$_7$S$_2$: C, 30.09; H, 1.77; S, 8.03. Observed: C, 30.22; H, 1.78; S, 8.08.

EXAMPLE XVII

Five hundred forty milligrams of benzofuran reacted according to the above procedure yielded 0.47 grams (47%) of 2,3-di[phenyl(trifluoromethanesulfonyloxy)iodo]-1,4-epoxy-1,4-diphenylnapthalone. The melting point was 93°-95° C. (dec). Spectral analysis was: IR (CCl$_4$, cm$^{-1}$): 3082, 3055, 1469, 1455, 1294, 1216, 1163, 1019, 987, 902. $^1$H NMR (δ, CD$_3$CN): 7.05–7.15 (m, 4H, C$_6$H$_4$), 7.3 (m, 1OH, 2Ph), 7.6–7.9 (m, 1OH, 2PhI+). $^{19}$F NMR (δ, CD$_3$CN): −76.52 (s, CF$_3$). $^{13}$C NMR (δ, CD$_3$CN): 98.5 (C-1 and C-4), 121.0 (quart. J=319 Hz, CF$_3$), 113.8, 123.8, 127.8, 128.4, 130.5, 131.6, 131.9, 133.5, 134.4, 136.8 (Aryl), 145.7 (C-2 and C-3), 150.1 (C-5 and C-10). Mass spectrum (FAB): m/z (%) 499 (25), [M+H$^+$−2 TfO$^-$−PhI]$^+$; 295 (100), [M+H$^+$−2 TfO$^+$−PhI]$^+$. HRMS for C$_{28}$H$_{19}$IO [M+H$^+$−2 TfO$^-$−PhI]$^+$: calculated value 499.05581, observed value 499.05581.

Various monofunctionalized acetylenes can also be synthesized from the (phenyliodonium) alkynyl sulfonates or the bis(phenyliodonium) alkynyl sulfonates. In one embodiment, the trifluoromethanesulfonate F' (reactions (2C) or (3)), are reacted with any of a wide range of nucleophilic and non-nucleophilic salts (reactions 11 and 12).

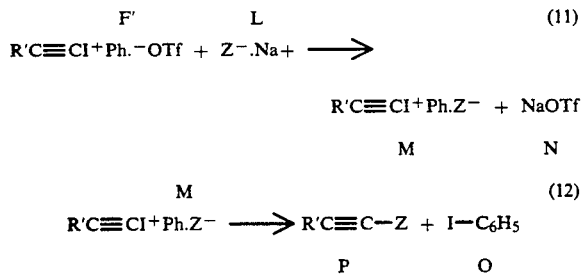

Reactions (11) and (12) provide a highly versatile pathway for synthesis of products P, depending only on product stability. The anion functional moieties Z which can be added may depend on the R' group of compound F' which is derived from the trialkyltin acetylene D'' in reactions (2C) or (3). For example, if R' is a carboxylate, Z may be hydrogen or any alkylcarboxylate, benzoate, alkylbenzoate, or methoxybenzoate. Amino-, nitro-, fluoro-, and sulfo-benzoates are also within contemplation. If R' is a sulfonate, Z may be hydrogen, alkyl, alkylphenyl, alkoxyphenyl, alkylaryl, nitrophenyl, toluene. When R'(Z?) is a phosphate, the phosphate may be an alkyl mono-, di-, or tri-ester, and any non-esterified oxygens of the phosphate may have a hydrogen or any cationic counterion bonded to them. Cationic counterions associated with the phosphate may include, but are not limited to, sodium, potassium, and tetraalkylammonium.

In reactions (11) and (12), Z may also be of low nucleophilicity, such as a nitrate, sulfonate, or perchlorate. When Z is a nitrate, the oxygen moieties thereof may also either be bonded with hydrogen or various cationic counterions including the above, or esterified to alkyl groups.

The monofunctionalized acetylene is produced by decomposition of compound M to yield the acetylene P and iodobenzene R (reaction (12)). In many cases, reaction (12) proceeds spontaneously to completion within a period of hours due to the instability of compound M, without heating or other additional stimuli. It is generally desirable to avoid heating or other harsh treatments because some of the products P are not stable to such treatments.

Products P are readily recovered by means of standard workup procedures, with yields generally around 80–90%. The byproduct Q, iodobenzene, may also be recovered and readily purified and recycled or used in other synthetic applications.

In some cases, particularly when Z is a group of low nucleophilicity such as sulfonate, nitrate or perchlorate, a metal catalyst may be required to facilitate the applications.

In some cases, particularly when Z is a group of low nucleophilicity such as sulfonate, nitrate or perchlorate, a metal catalyst may be required to facilitate the decomposition reaction (12). Metal catalysts suitable for this purpose include triflates such as copper triflate, silver triflate, copper or silver tosylates, and others.

An alternate method of performing reaction (11) involves the use of an ion exchange resin such as Amberlyst. In this case, a resin column is loaded with the salt of the desired anion, e.g. sodium benzoate in the example just given. The alkynyl(phenyliodonium)salt is its solvent, for example methylene chloride. The subsequent decomposition, reaction (12), is then performed in the manner described.

EXAMPLE XVIII 3,3-Dimethyl-1-butynyl(phenyl)iodonium trifluoromethanesulfonate (4.34 grams, 10 millimoles, dissolved in 10 milliliters of methylene chloride was reacted with sodium tosylate (9.8 grams, 50 millimoles) dissolved in 20 milliliters of water. The reactants were stirred for 5 minutes at 0° C. The organic layer was concentrated and diethyl ether was added, precipitating the product. The yield was 3.75 grams or 76% of a crystalline solid with a melting point of 120°-122° C(dec). Analysis by infrared and multinuclear NMR spectral methods identified the product as 3,3-dimethyl-1-butynyl(phenyl)iodonium tosylate.

EXAMPLE XIX

Iodosobenzene (2 42 grams, 11 millimoles) was reacted with trimethylsilyl trifluoromethanesulfonate (2.13 milliliters, 11 millimoles) in 15 milliliters of methylene chloride for 10 minutes. 1-Trimethyl-silyl-3,3-dimethyl-1-butyne (2.2 milliliters, 10 millimoles) dissolved in 15 milliliters of methylene chloride was then added and the reactants were further incubated at 0° C. for 30 minutes. The solution was then stirred with aqueous sodium nitrate (4.3 grams dissolved in 30 milliliters of water) for 5 minutes, and the organic layer was concentrated by evaporation. Upon addition of diethyl ether, the product 3,3-dimethyl-1-butynyl(phenyl)iodonium nitrate was precipitated as crystals with a melting point of 86°-87° C.(dec). The yield was 3.47 grams or 93%. After additional washing with ether the product was identified by infrared and multinuclear NMR spectral analysis.

EXAMPLE XX

Ethynyl(phenyl)iodonium trifluoromethanesulfonate (3.78 grams, 10 millimoles) dissolved in 10 milliliters of methylene chloride was mixed with sodium benzoate (7.2 grams, 50 millimoles) dissolved in 20 milliliters of water. The reactants were stirred for 5 minutes at 0° C. The organic layer was concentrated by evaporation and chromatographed on silica gel columns to isolate 0.77 grams of ethynyl benzoate (53% yield). The product was identified by spectroscopic means, and had a melting point of 43° C.(dec).

EXAMPLE XXI

1-Hexynyl(phenyl)iodonium trifluoromethanesulfonate (4.34 grams, 10 millimoles) dissolved in methylene chloride was mixed with sodium diethylphosphate (8.8 grams, 50 millimoles) dissolved in water. The reactants were stirred for 5 minutes at 0° C. Infrared spectral analysis revealed the presence of hexynyl(phenyl)iodonium diethylphosphate, which decomposed to 1-hexynyl 1-diethylphosphate after 24 hours. Although the presence of the desired compound has been demonstrated by the spectral analysis, difficulties in its isolation in a pure form have not yet been overcome.

In an alternate embodiment, 1,3-diynyliodonium trifluoromethanesulfonates can also be reacted with nucleophiles in a manner analogous to reactions (11) and (12). Reaction (13) with triphenyl phosphine is an example:

R''C≡C—C≡CI+Ph.−OTf +     (13)

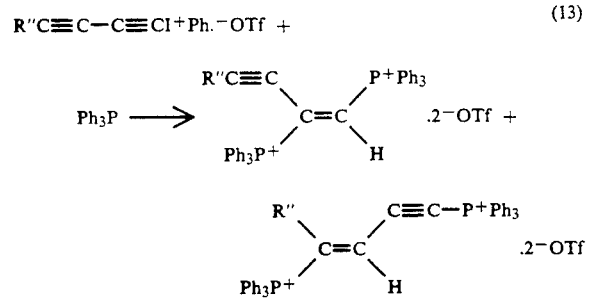

From the ready reaction of the diynyliodonium triflate with triphenylphosphine, it is believed that the compound will also react with other nucleophiles to produce functionalized diacetylenes of the general structure

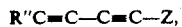

where Z may be any of the nucleophilic moieties discussed herein which yields a stable product.

EXAMPLE XXII 5,5-dimethyl-1,3-hexadiynyl(phenyliodonium) trifluoromethanesulfonate (0.88 grams, 1.75 millimoles) was added to 50 milliliters of toluene and cooled to −78° C. under nitrogen. Triphenylphosphine (0.92 grams, 3.5 millimoles) dissolved in 5 milliliters of toluene was added dropwise. The mixture was stirred at −78° C. for 10 minutes, and then allowed to warm to room temperature. The mixture was stirred for another 10 minutes at room temperature, and ether was added to separate out an oil. The oil was washed twice with additional ether. Crystallization from dichloromethane/ether yielded white crystals that were washed first with toluene, then with ether to remove unreacted triphenylphosphine. Recrystallization yielded a product 5,5-dimethyl-1,2-bis(triphenylphosphonio)hex-3-yne-1-ene ditriflate, having a melting point of 182° C. Another isomer, 5,5-dimethyl-1,4-bis(triphenylphosphonio)hex-3-yne-1-ene ditriflate having a melting point of 137°–140° C., was obtained by adding hexane to the mother liquor. Double recrystallization of the second product was required to remove small amounts of the first product and other byproducts. The total yield was 31% of products 1 and 2 in a 3:2 ratio. The identities of both products were confirmed by IR and NMR spectroscopy.

Although specific embodiments of composition, of conditions for performing the synthetic reactions, and of recovery of the products have been described herein, it is to be understood that the invention is not limited by these embodiments. For example, the 'standard workup procedures' for recovery of the products from reactions (2B), (2C), and (3)–(13) may include crystallization, evaporation, column chromatography, distillation, sublimation, etc., as required by the nature of various products. Similarly, the solvents and other conditions for Reactions 1–10 may be modified according to the requirements of specific reactants and products.

The research which produced these compounds and products was performed at the University of Utah and was substantially funded by National Institutes of Health grant #5-RO1-CA16903 to Peter Stang.

What is claimed is:

1. A mixed iodonium sulfonate compound having the structure

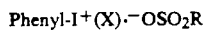

wherein R is selected form the group consisting of —CF₃, n-C₄F₉, and p-CH₃C₆H₄; and X is selected from the group consisting of OAc, NHAc, NCO, CN, and C≡CR'; wherein R' may be any one of the following, a lower alkyl group, a phenyl group, a halogen, a keto, arylketo, alkylketo, amidoketo, esterified keto, arylsulfone group, an amino group, an alkoxy group where the alkyl is a lower alkyl group, a silyl or tri-alkylsilyl where the alkyl is a lower alkyl group, an alkyl-O-CH₂ where the alkyl is a lower alkyl group, or an arylalkyl group or arylaklyl substituted with a functional group selected from the class consisting of a lower alkyl group, a phenyl group, a halogen, an amino group, a nitrate group, or a sulfonate group.

2. The compound of claim 1, wherein R is —CF₃ and X is CN.

3. The compound of claim 1, wherein R is −CF₃ and X is C≡CR'.

4. A mixed iodonium sulfonate compound having the structure

wherein R' is H or any R' moiety which can be derived by the following reaction:

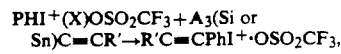

wherein X is OAc, NHAc, NCO, or CN, and wherein A is selected from the group consisting of: n- butyl, methyl, ethyl, phenyl.

5. The compound of claim 4, wherein R' wherein R' may be any one of the following: a lower alkyl group; a phenyl group; a halogen; a keto, arylketo, alkylketo, amidoketo, esterified keto, or arylsulfone group; an amino group; an alkoxy group where the alkyl is a lower alkyl group; a silyl or tri-alkylsilyl where the alkyl is a lower alkyl group; an alkyl-O-CH$_2$ where the alkyl is a lower alkyl group; or an arylalkyl group or arylalkyl substituted with a functional group which may be a lower alkyl group, a phenyl group, a halogen, an amino group, a nitro- or nitroso-group, a carboxyl group, or a sulfonate group.

6. A method of making a mixed iodonium sulfonate, comprising the steps of:

perparing a solution comprising an organic solvent, iodosobenzene, and a tri-alkylsily sulfonate having the gneral structure A$_3$Si-OSO$_2$R with A being a lower alkyl and R being selected from the group consisting of: —CF$_3$, n-C$_4$F$_9$, and p-CH$_3$C$_6$H$_4$;

reacting the solution for a time sufficient to produce an intermediate solution;

adding to the intermediate solution a trialkylsilyl compound having the structure A'$_3$SiX, wherein X is selected from the group consisting of: OAc, NHAc, NCO, and CN, and A' is a lower alkyl;

further reacting the intermediate solution after addition of the trialkylsilyl compound for a sufficient time to form a precipitate containing a mixed iodonium sulfonate having the structure Phenyl-I$^+$(X)·OSO$_2$R;

and recovering the mixed iodonium sulfonate.

7. The method of claim 6, wherein the solution is prepared at a temperature below about −20° C., and the step of reacting the solution is performed at a temperature between about 0° and about −10° C.

8. The method of claim 7, further including a step of cooling said intermediate solution to below about −20° C. prior to said step of adding a trialkylsilyl compound.

9. The method of claim 8, wherein said step of reacting said intermediate solution with said trialkylsilyl compound is performed at a temperature between about 0° C. and −10° C.

10. The method of claim 6, wherein the mixed iodonium sulfonate is stable under normal conditions.

11. A mixed iodonium sulfonate compound having the structure

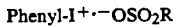

Phenyl-I$^{+}$·$^{-}$OSO$_2$R wherein R is selected from the group consisting of —CF$_3$, n-C$_4$F$_9$, and p-CH$_3$C$_6$H$_4$; and X is selected from the group consisting of OAc, NHAc, NCO, CN, and C≡Cr'; wherein R' may be any one of the following, a lower alkyl group; an phenyl group, a halogen, a keto, arylketo, alkylketo, amidoketo, esterified keto, arylsulfone group, an amino group, an alkoxy group where the alkyl is a lower alkyl group, a silyl or tri-alkylsilyl where the alkyl is a lower alkyl group, an alkyl-O-CH$_2$ where the alkyl is a lower alkyl group, or an arylalkyl group.

* * * * *